United States Patent

Haase et al.

Patent Number: 5,962,452
Date of Patent: Oct. 5, 1999

[54] RESORCINYL-TRIAZINES

[75] Inventors: Jürg Haase, Bettingen, Switzerland; Helmet Luther, Grenzach-Wyhlen, Germany

[73] Assignee: Ciba Specialty Chemicals Corporation, Tarrytown, N.Y.

[21] Appl. No.: 09/078,928

[22] Filed: May 14, 1998

[30] Foreign Application Priority Data

May 16, 1997 [EP] European Pat. Off. .............. 97810304

[51] Int. Cl.⁶ ........................ G03C 1/815; C07D 251/12; A61K 7/42
[52] U.S. Cl. .......................... 514/241; 424/401; 544/215; 544/216
[58] Field of Search ..................... 544/215, 216; 424/401, 59; 514/241

[56] References Cited

U.S. PATENT DOCUMENTS

| | | | |
|---|---|---|---|
| 3,444,164 | 5/1969 | Luethi et al. | 260/248 |
| 3,843,371 | 10/1974 | Piller et al. | 96/84 R |
| 4,826,978 | 5/1989 | Migdal et al. | 544/216 |
| 5,300,414 | 4/1994 | Leppard et al. | 430/507 |
| 5,601,811 | 2/1997 | Gallagher et al. | 424/709 |

FOREIGN PATENT DOCUMENTS

| | | |
|---|---|---|
| 0165608 | 12/1985 | European Pat. Off. . |
| 0531258 | 3/1993 | European Pat. Off. . |
| 0743309 | 11/1996 | European Pat. Off. . |
| 2084822 | 12/1971 | France . |
| 484695 | 3/1970 | Switzerland . |
| 1061521 | 3/1967 | United Kingdom . |
| 2273498 | 6/1994 | United Kingdom . |
| 9418278 | 8/1994 | WIPO . |
| 9522959 | 8/1995 | WIPO . |
| 9703643 | 2/1997 | WIPO . |

*Primary Examiner*—Mukund J. Shah
*Assistant Examiner*—Pavanaram K Sripada
*Attorney, Agent, or Firm*—Kevin T. Mansfield

[57] ABSTRACT

Resorcinyl-triazines of formula

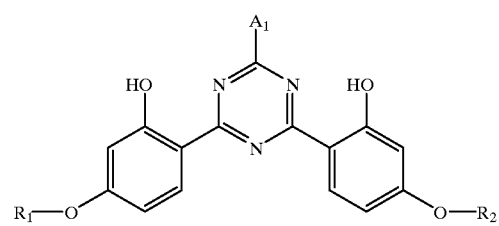

are described. The compounds according to the invention are suitable especially as sunscreens in cosmetic, pharmaceutical and veterinary compositions.

9 Claims, No Drawings

RESORCINYL-TRIAZINES

The present invention relates to novel resorcinyl-triazines, to processes for the preparation of those compounds and to the use of selected resorcinyl-triazines for cosmetic compositions.

The novel resorcinyl-triazines correspond to formula

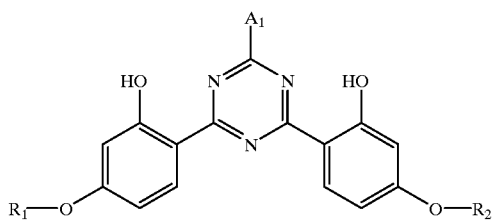

(1)

wherein $R_1$ and $R_2$ are each independently of the other a radical of formula (1a)

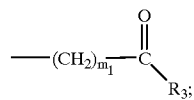

(1a)

$R_3$ is hydroxy; $C_1$–$C_5$alkyl that is unsubstituted or substituted by one or more OH groups; $C_1$–$C_5$alkoxy; amino; mono- or di-$C_1$–$C_5$alkylamino; M; a radical of formula

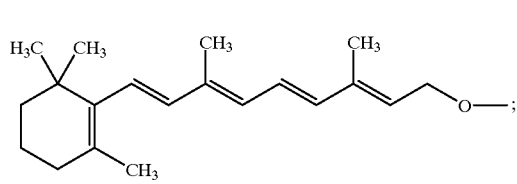

(1b)

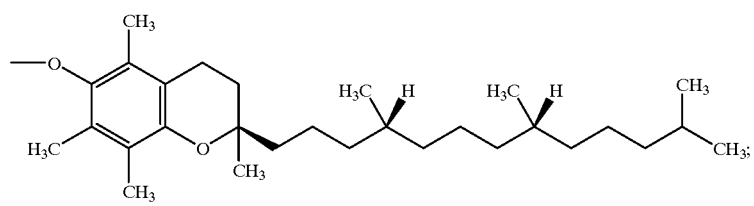

(1c)

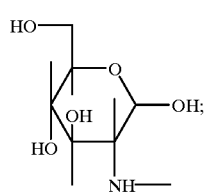

(1d)

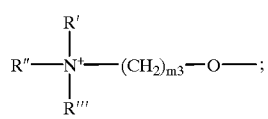

(1e)

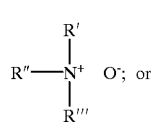

(1f)

-continued

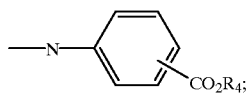

wherein R', R" and R'" are each independently of the others $C_1$–$C_{14}$alkyl that is unsubstituted or substituted by one or more OH groups;

$R_4$ is hydrogen; M; $C_1$–$C_5$alkyl; or a radical of the formula —$(CH_2)_{m_2}$—O—$T_1$;

$A_1$ is a radical of formula

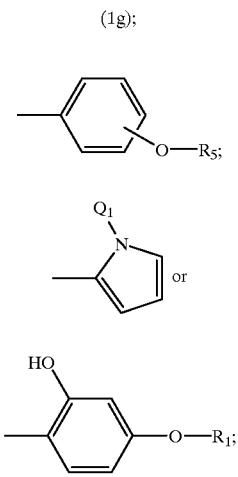

$R_5$ is hydrogen; $C_1$–$C_{10}$alkyl, —$(CH_2CHR_6$—O$)_{n_1}$—$R_4$, or a radical of the formula —$CH_2$—CH(—OH)—$CH_2$—O—$T_1$;

$R_6$ is hydrogen; or methyl;

$T_1$ is hydrogen; or $C_1$–$C_8$alkyl;

$Q_1$ is $C_1$–$C_{18}$alkyl;

M is a metal cation;

$m_1$ is from 1 to 3; and $m_2$ is from 1 to 4;

$m_3$ is from 2 to 14; and $n_1$ is 1–16.

$C_1$–$C_5$Alkyl, $C_1$–$C_8$alkyl, $C_1$–$C_{10}$alkyl and $C_1$–$C_{18}$alkyl are straight-chain or branched alky radicals, for example methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl, penta-decyl, hexadecyl, heptadecyl or octadecyl.

$C_1$–$C_5$Alkoxy are straight-chain or branched radicals, for example methoxy, ethoxy, n-pro-poxy, isopropoxy, n-butoxy, sec-butoxy, tert-butoxy, amyloxy, isoamyloxy or tert-amyloxy.

Examples of mono- or di-$C_1$–$C_5$alkylamino are methylamino, ethylamino, propylamino, n-butylamino, sec-butylamino, tert-butylamino, pentylamino, dimethylamino, diethylamino; dipropylamino; dibutylamino or methyl-ethylamino.

Examples of metal cations are the lithium, potassium, sodium, calcium, magnesium, copper or zinc ion.

Preference is given to resorcinyl compounds of formula (1) wherein $A_1$ is a radical of formula

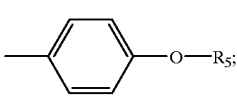

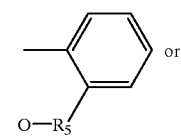

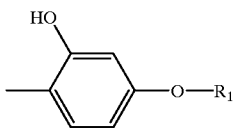

wherein $R_1$ and $R_5$ are as defined for formulae (1h) and (1k).

Important resorcinyl compounds according to the invention correspond to formula

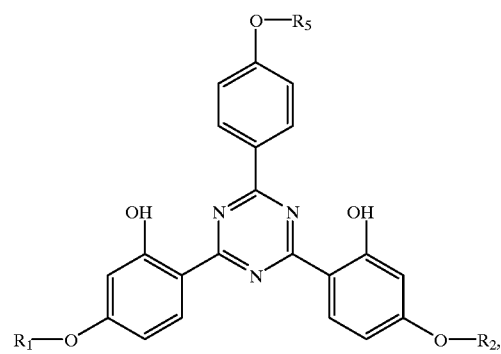

wherein $R_1$ and $R_2$ are each independently of the other a radical of the formula

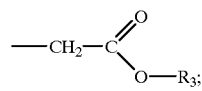

$R_3$ is hydrogen; or $C_1$–$C_5$alkyl; and $R_5$ is $C_1$–$C_{10}$alkyl.

Further important resorcinyl-triazine compounds correspond to formula

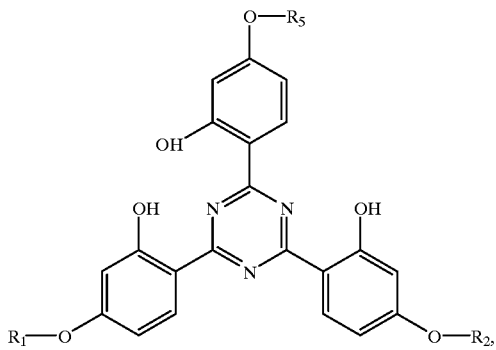 (3)
wherein
$R_1$, $R_2$ and $R_5$ are each independently of the others a radical of the formula
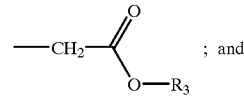 ; and
$R_3$ is hydrogen; or $C_1$–$C_5$alkyl.
Special preference is given to compounds of formula (3) wherein $R_1$, $R_2$ and $R_5$ have the same meaning.
Examples of triazine derivatives according to the invention are given in Table 1:

TABLE 1

| $R_a$ | $R_b$ | $R_c$ |
|---|---|---|
| $CH_3$ | $-C(CH_3)_3$ | $-C(CH_3)_3$ |
| $C_2H_5$ | $-C(CH_3)_3$ | $-C(CH_3)_3$ |
| $CH_3$ | 4-($CH_3$NH)-$C_6H_4$-$COOC_4H_9$ | 4-($CH_3$NH)-$C_6H_4$-$COOC_4H_9$ |
| $C_2H_5$ | 4-($CH_3$NH)-$C_6H_4$-$COOC_4H_9$ | 4-($CH_3$NH)-$C_6H_4$-$COOC_4H_9$ |
| $CH_3$, $C_2H_5$, $-OH$ | $-OH$, $-OH$, $-OH$ | $-OH$, $-OH$, $-OH$ |

TABLE 1-continued

[Structure: central triazine (pyrimidine-like) ring with three aryl substituents: one 4-(O—Ra)phenyl group, and two 2-hydroxy-4-(O—CH₂—C(=O)—R_b or R_c)phenyl groups]

| $R_a$ | $R_b$ | $R_c$ |
|---|---|---|
| CH₃ | —OM<br>M = alkali, alkaline earth, Cu, Zn, Mg | —OM<br>M = alkali, alkaline earth, Cu, Zn, Mg |
| C₂H₅ | —OM<br>M = alkali, alkaline earth, Cu, Zn, Mg | —OM<br>M = alkali, alkaline earth, Cu, Zn, Mg |
| CH₃ | O⁻·⁺N(CH₂CH₂OH)₃ | O⁻·⁺N(CH₂CH₂OH)₃ |
| C₂H₅ | O⁻·⁺N(CH₂CH₂OH)₃ | O⁻·⁺N(CH₂CH₂OH)₃ |
| CH₃ | $O^- \cdot {}^+N(CH_3)_2(CH_3)$—(CH₂)ₙ—O—, n = 2–14 | $O^- \cdot {}^+N(CH_3)_2(CH_3)$—(CH₂)ₙ—O—, n = 2–14 |
| C₂H₅ | $O^- \cdot {}^+N(CH_3)_2(CH_3)$—(CH₂)ₙ—O—, n = 2–14 | $O^- \cdot {}^+N(CH_3)_2(CH_3)$—(CH₂)ₙ—O—, n = 2–14 |
| CH₃ | —O—CH₂—CH(OH)—CH₂CH₃ (2-hydroxybutoxy) | —O—CH₂—CH(OH)—CH₂CH₃ (2-hydroxybutoxy) |

TABLE 1-continued
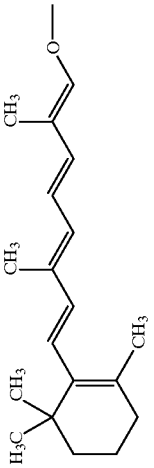

TABLE 1-continued
| $R_a$ | $R_b$ | $R_c$ |
|---|---|---|
| CH$_3$ |  | 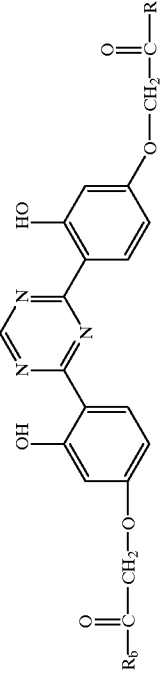 |
| C$_2$H$_5$ | 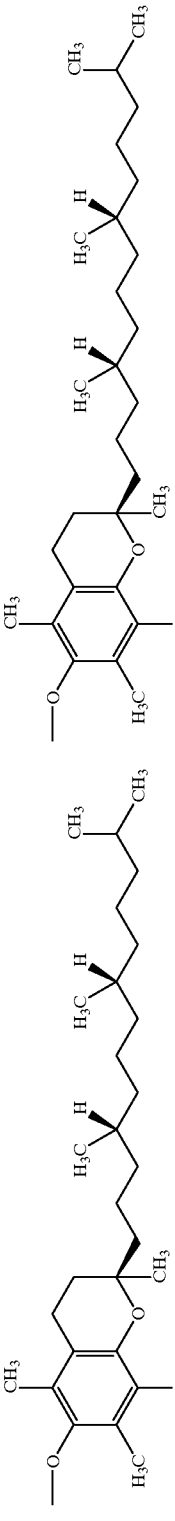 | 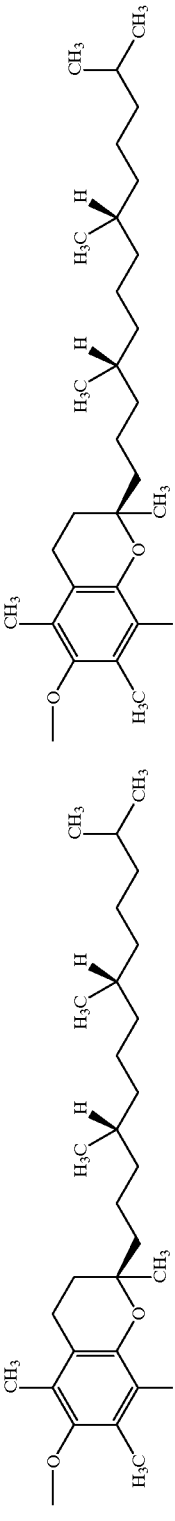 |
| CH$_3$ |  | 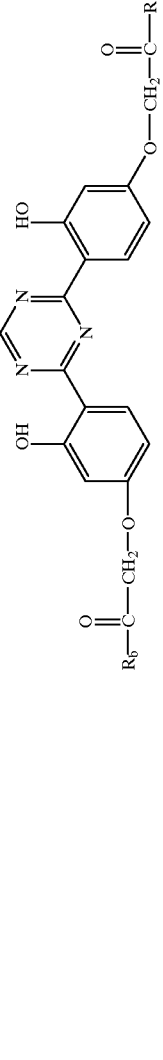 |
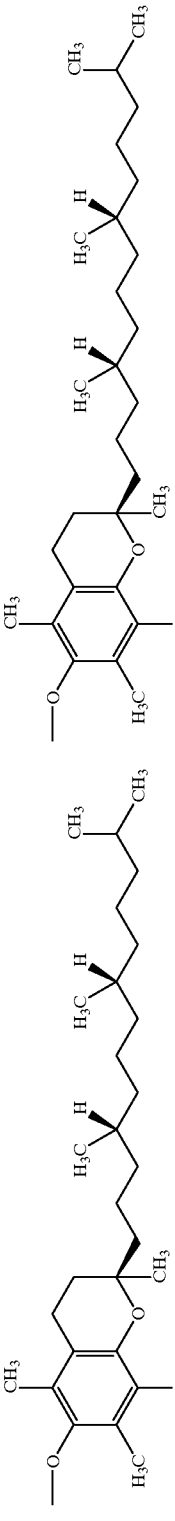

TABLE 1-continued
| $R_a$ | $R_b$ | $R_c$ |
|---|---|---|
| $C_2H_5$ |  | |

The novel resorcinyl-triazines can be prepared in various ways.

For example, compounds of formula (1) wherein $A_1$ is a radical of formula (1h) and $R_1$ and $R_2$ have the same meaning can be prepared in a three-step reaction, starting from cyanuric chloride. In that reaction the appropriate phenylmagnesium bromide compound is reacted in a Grignard reaction with cyanuric chloride to form a dichlorotriazine compound of formula

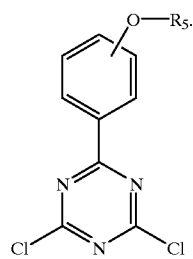

(1l)

Processes for the preparation of that intermediate are known and are described, for example, in EP-A-0 577 559. The two resorcinol groups are then introduced in a generally known manner by Friedel-Crafts acylation of resorcinol in the presence of a Lewis acid, especially aluminium chloride. In the third step, the etherification of the free, p-positioned hydroxy groups is effected, depending upon the meaning of the radicals $R_1$ and $R_2$, by alkylation or acid-catalysed addition of glycidyl ethers. Detailed information in this connection can be found in the Preparation Examples.

The dichlorotriazine intermediate of formula (1l) can also be obtained without the use of Grignard reagents by a ring-closure reaction. For that purpose, the appropriately substituted benzonitrile is reacted with dicyanodiamide to form 6-aryl-1,3,5-triazine-2,4-dione, which is converted with thionyl chloride into the chlorine derivative of formula (1l). Alternatively, the compound of formula (1l) can be obtained also by reaction of the appropriately substituted N,N-dimethyl-carboxylic acid amides with phosphorus oxychloride and N-cyano-chloro-formamidine. Those reactions are already known and are described, for example, in Dyes and Pigments 7, 419–443 (1986).

Compounds of formula (1) wherein $A_1$ is a radical of formula (1h) can be obtained also by reaction of phenyl-substituted benzoxazin-4-ones of formula

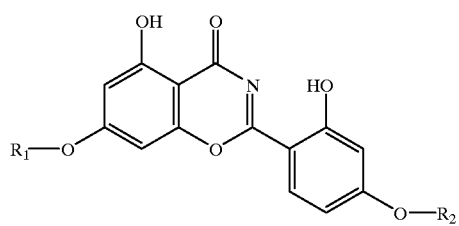

(1m)

with benzamidine compounds of formula

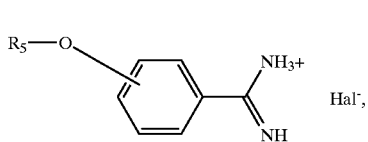

(1n)

wherein $R_1$, $R_2$ and $R_5$ are as defined for formula (1). The preparation of such benzoxazinone intermediates and the reaction with amidines are described in Helv. Chim. Acta 55, 1566–1595 (1972).

When, in formula (1), $A_1$ is a radical of formula (1g) and $R_1$ and $R_2$ have the same meaning, the resorcinyl-triazines according to the invention can be prepared, for example, in a three-step reaction, starting from cyanuric chloride. In that reaction the appropriate aminobenzoic acid ester is reacted with cyanuric chloride to form a dichlorotriazine compound of formula

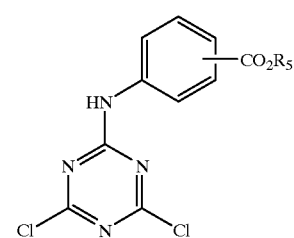

(10)

The two resorcinol groups are then introduced in a generally known manner by Friedel-Crafts acylation of resorcinol in the presence of a Lewis acid, especially aluminium chloride. Those reactions are described, for example, in EP-A-165 608. Finally, the etherification of the free, p-positioned hydroxy groups is effected, depending upon the meaning of the radicals $R_1$ and $R_2$, by alkylation or acid-catalysed addition of glycidyl ethers. Detailed information in this connection can be found in the Synthesis Examples.

The compounds of formula (1) according to the invention can also be prepared by dehydrogenation of a dihydrotriazine compound of formula

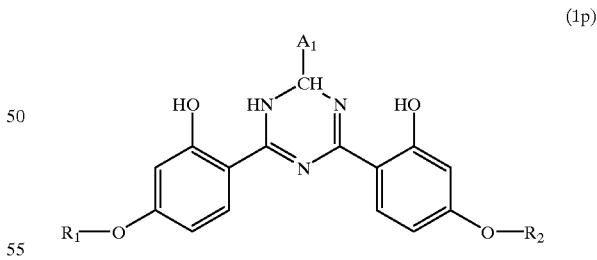

(1p)

wherein $R_1$, $R_2$ and $A_1$ are as defined for formula (1).

The dehydrogenation agent used is generally chloranil. The dehydrogenation of dihydro-triazine compounds to form 1,3,5-triazines with the aid of chloranil is known, for example, from Khim. Geteritsikl. Soedin. (2), p. 350–353 (1969).

Compounds of formula (1) wherein $A_1$ is a radical of formula (1l) and $R_1$ and $R_2$ have the same meaning can be prepared, for example, in a three-step reaction, starting from cyanuric chloride. In that reaction the appropriate N-alkylpyrrole is reacted with cyanuric chloride in a Friedel- Crafts reaction selectively to form the dichlorotriazine compound of formula

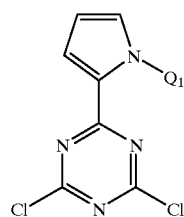

(1q)

wherein $Q_1$ is as defined for formula (1).

The two resorcinol groups are then introduced in a generally known manner by Friedel-Crafts acylation of resorcinol in the presence of a Lewis acid, especially aluminium chloride. Those reactions are described, for example, in EP-A-165 608. The etherification of the free, p-positioned hydroxy groups is effected by alkylation or acid-catalysed addition of glycidyl ethers. Detailed information in this connection can be found in the Synthesis Examples.

The compounds of formula (1) according to the invention are suitable especially as UV filters, that is to say for protecting ultraviolet-sensitive organic materials, especially for protecting the skin and hair of human beings and animals against the damaging effect of UV radiation. Those compounds are therefore suitable as light-stabilisers in cosmetic, pharmaceutical and veterinary compositions. The compounds can be used both in dissolved form and in a micronised state.

The invention therefore relates also to a cosmetic composition comprising at least one compound of formula (1) as well as cosmetically acceptable carriers or auxiliaries.

For cosmetic use, the light-stabilisers according to the invention usually have an average particle size in the range of from 0.02 to $2\mu$, preferably from 0.05 to $1.5\mu$, and especially from 0.1 to $1.0\mu$. The insoluble UV absorbers according to the invention can be brought to the desired particle size by customary methods, e.g. grinding using a jet mill, ball mill, vibratory mill or hammer mill. The grinding is preferably carried out in the presence of from 0.1 to 30% by weight, especially from 0.5 to 15% by weight, based on the UV absorber, of a grinding aid, for example an alkylated vinylpyrrolidone polymer, a vinylpyrrolidone-vinyl acetate copolymer, an acyl glutamate or especially a phospholipid.

In addition to the UV absorber according to the invention, the cosmetic composition may also comprise one or more further UV screening agents of the following classes of substance:

1. p-aminobenzoic acid derivatives, e.g. 4-dimethylaminobenzoic acid 2-ethylhexyl ester;
2. salicylic acid derivatives, e.g. salicylic acid 2-ethylhexyl ester;
3. benzophenone derivatives, e.g. 2-hydroxy-4-methoxybenzophenone and the 5-sulfonic acid derivative thereof;
4. dibenzoylmethane derivatives, e.g. 1-(4-tert-butylphenyl)-3-(4-methoxyphenyl)propane-1,3-dione;
5. diphenylacrylates, e.g. 2-ethylhexyl-2-cyano-3,3-diphenylacrylate and 3-(benzofuranyl)-2-cyanoacrylate;
6. 3-imidazol-4-yl-acrylic acid and esters;
7. benzofuran derivatives, especially 2-(p-aminophenyl)benzofuran derivatives, described in EP-A-582 189, U.S. Pat. No. 5,338,539, U.S. Pat. No. 5,518,713 and EP-A-613 893;
8. polymeric UV absorbers, e.g. the benzylidene malonate derivatives described in EP-A-709 080;
9. cinnamic acid derivatives, e.g. the 4-methoxycinnamic acid 2-ethylhexyl ester and isoamyl ester or cinnamic acid derivatives disclosed in U.S. Pat. No. 5 601 811 and WO 97/00851;
10. camphor derivatives, e.g. 3-(4'-methyl)benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylene-dimethine)-bis(7,7-dimethyl-2-oxo-bicyclo[2.2.1]heptane-1-methanesulfonic acid) and salts, 3-(4'-sulfo)benzylidene-bornan-2-one and salts;
11. trianilino-s-triazine derivatives, e.g. 2,4,6-trianiline-(p-carbo-2'-ethyl-1'-oxy)-1,3,5-triazine and the UV absorbers disclosed in U.S. Pat. No. 5,332,568, EP-A-517 104, EP-A-507 691, WO 93/17002 and EP-A-570 838;
12. 2-hydroxyphenyl-benzotriazole derivatives;
13. 2-phenylbenzimidazole-5-sulfonic acid and salts thereof;
14. menthyl-o-aminobenzoate;
15. $TiO_2$ (variously coated), ZnO and mica.

The UV absorbers described in "Sunscreens", Eds. N. J. Lowe, N. A. Shaath, Marcel Dekker, Inc., New York and Basle or in Cosmetics & Toiletries (107), 50ff (1992) can also be used as additional UV screening agents in the formulation according to the invention.

Furthermore, the cosmetic composition according to the invention can be used also together with known anti-oxidants, e.g. vitamin E, carotinoids or HALS (="Hindered Amine Light Stabilizer") compounds.

The cosmetic composition according to the invention contains from 0.1 to 15% by weight, preferably from 0.5 to 10% by weight, based on the total weight of the composition, of a UV absorber or a mixture of UV absorbers, and a cosmetically acceptable auxiliary.

The preparation of the cosmetic composition can be effected by physically mixing the UV absorber(s) with the auxiliary by customary methods, for example by simply stirring the individual components together.

The cosmetic composition according to the invention can be formulated as a water-in-oil or oil-in-water emulsion, an oil-in-alcohol lotion, a vesicular dispersion of an ionic or non-ionic amphiphilic lipid, a gel, a solid stick or an aerosol formulation.

As a water-in-oil or oil-in-water emulsion, the cosmetically acceptable auxiliary preferably contains from 5 to 50% oily phase, from 5 to 20% emulsifier and from 30 to 90% water. The oily phase may contain any oil suitable for cosmetic formulations, e.g. one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

Any conventionally usable emulsifier can be used for the cosmetic composition according to the invention, for example one or more ethoxylated esters of natural derivatives, e.g. poly-ethoxylated esters of hydrogenated castor oil; or a silicone oil emulsifier, e.g. a silicone polyol; an optionally ethoxylated fatty acid soap; an ethoxylated fatty alcohol; an optionally ethoxylated sorbitan ester; an ethoxylated fatty acid; or an ethoxylated glyceride.

The cosmetic composition may also comprise further components, e.g. emollients, emulsion stabilisers, skin humectants, skin tanning accelerators, thickeners, such as xanthan, moisture-retention agents, such as glycerol, preservatives, perfumes and colourings.

The cosmetic composition according to the invention is distinguished by excellent protection of human skin against the damaging effect of sunlight.

In the Examples that follow, percentages relate to weight. In the case of the resorcinyl-triazine compounds used, the amounts relate to the pure substance.

Preparation Examples for the Novel Compounds

EXAMPLE 1

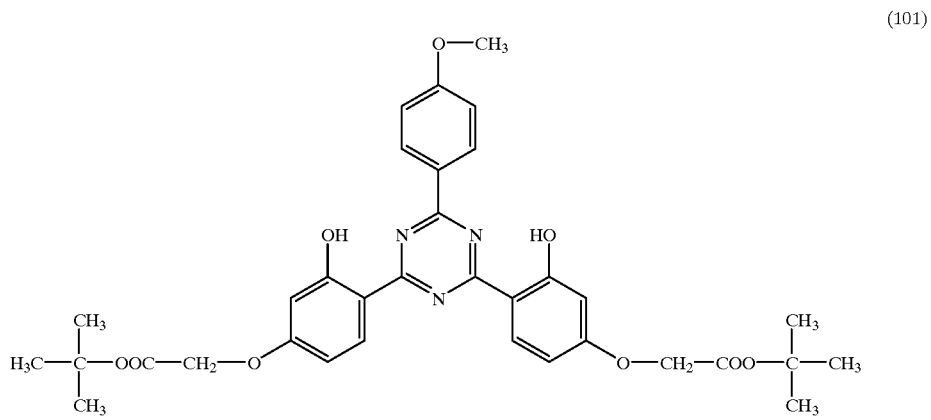

(101)

5.05 g of 2,4-bis(2,4-dihydroxyphenyl)-6-(4-methoxyphenyl)-1,3,5-triazine, 40 g of dimethyl-formamide (DMF) and 5.1 g of sodium methanolate solution (30%) are placed in a reactor and heated to 95° C. in vacuo. Approximately 10 g of DMF/methanol mixture are distilled off; the vacuum is relieved with nitrogen and then a solution of 3.96 g of tert-butyl chloroacetate in 10 g of DMF is added with thorough stirring. The reaction mixture is stirred at 90° C. for 12 hours. The reaction mass is then concentrated in a rotary evaporator and the semi-solid residue is extracted with acetone. A solution of the crude product in acetone is concentrated in vacuo and the residue is recrystallised 2× using a toluene/cyclohexane (17.5:12.5) mixture.

Yield: 2.6 g of yellow crystals
M.p.:88 to 94° C.

EXAMPLE 2

In accordance with Example 1, 6.95 g of 4-chloroacetamido-n-butyl benzoate are used instead of tert-butyl chloroacetate.

Working up is effected by extraction of the crude product with dioxane/water and methoxyethanol.

The compound of formula (102) is obtained

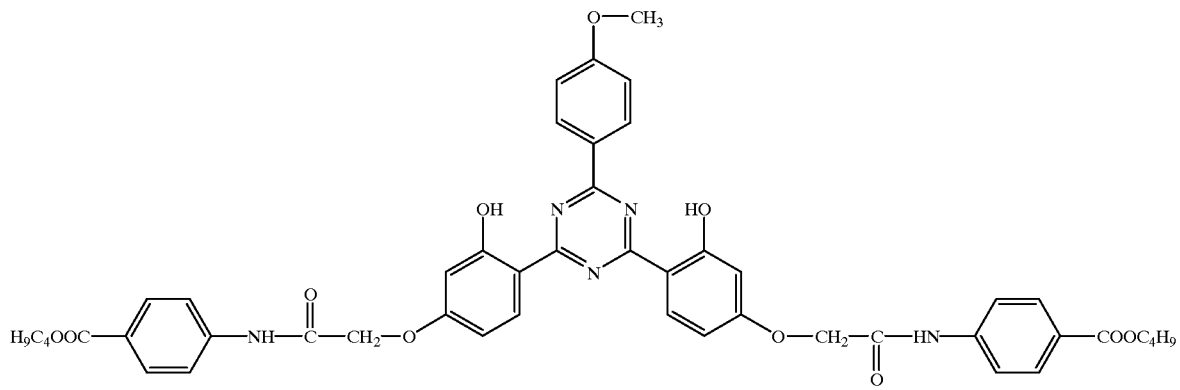

Yield: 5.5 g of yellow crystals
M.p.: 280° C.

| Elemental analysis: | C | N |
|---|---|---|
| calculated | 66.28% | 8.0% |
| found | 66.2% | 8.0% |

UV spectrum (measured in DMF):
$\lambda_{max1}$:286 nm; $\epsilon$=57 800
$\lambda_{max2}$:338 nm; $\epsilon$=49 600

EXAMPLE 3a 22.3 g of trisresorcinyl-triazine are reacted with 16.8 g of methyl chloroacetate using sodium methanolate (30%) as base in DMF in accordance with Example 1. The crude product is recrystallised from dioxane/methoxyethanol (1:1 mixture).

Yield: 9 g of trisresorcinyl-monoglycolic acid methyl ester.

EXAMPLE 3b
Hydrolysis to the Tricarboxylic Acid 9 g of the resulting methyl ester are stirred at reflux for 6 hours in a mixture consisting of 150 ml of 1N NaOH and 50 ml of dioxane. After cooling, the reaction mass is adjusted with HCl to a pH value of 3.0. The tricarboxylic acid of formula

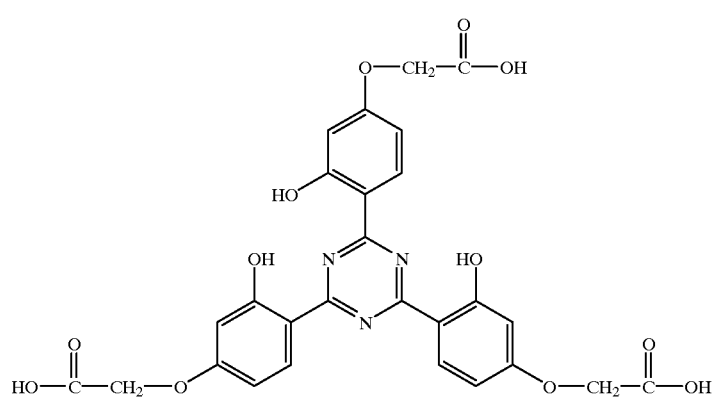

(103)

slowly separates out from the solution in the form of the trihydrate.

Yield: 3 g of grey powder

| Elemental analysis: | C | N |
|---|---|---|
| calculated | 51.2% | 6.6% |
| found | 50.5% | 6.3% |

UV spectrum (measured in DMF):

$\lambda_{max1}$:300 nm; $\epsilon$=27 700

$\lambda_{max2}$:348 nm; $\epsilon$=44 300

EXAMPLE 4a 40.0 g of 2,4-bis(2,4-dihydroxyphenyl)-6-(4-methoxyphenyl)-1,3,5-triazine are dissolved in 750 ml of DMF; 21.8 g of NaHCO$_3$ are added and, with stirring, the mixture is heated to 121° C. under reduced pressure (420 mbar). Over a period of about 3 hours, approximately 100 ml of DMF/water are distilled off from the reaction mass. After cooling to 20° C., the vacuum is relieved and, with stirring, 33 g of ethyl chloroacetate dissolved in 150 ml of DMF are slowly added dropwise. Stirring is continued at room temperature for 12 hours to complete the reaction and the reaction mass is then heated to 80° C. The suspension is filtered and, after the addition of 3 g of formic acid, concentrated under a high vacuum. The evaporation residue is extracted with methyl ethyl ketone, yielding 34 g of the compound of formula

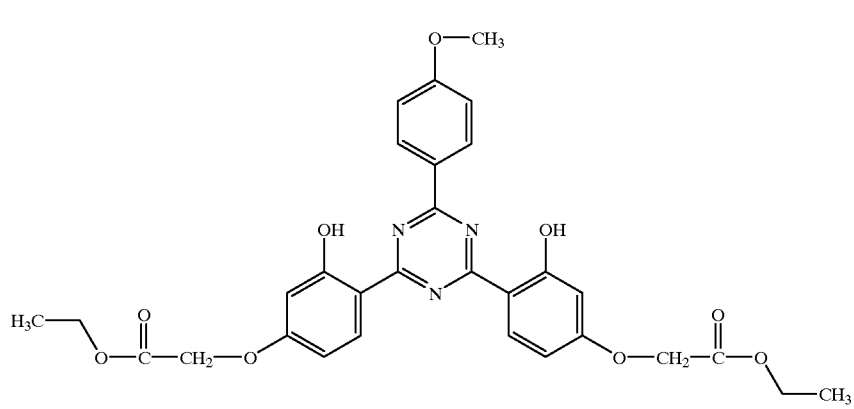

(104a)

EXAMPLE 4b

Hydrolysis of the Compound of Formula (104a)

22.5 g of the compound of formula (104a) are stirred in 50 ml of water and 50 ml of 2N NaOH for 10 hours at 95° C. The orange-red solution is cooled to 20° C. and then 100 ml of 1N HCl are added thereto. The free acid precipitates. The filter residue is dried in vacuo, yielding about 20 g of the compound of formula

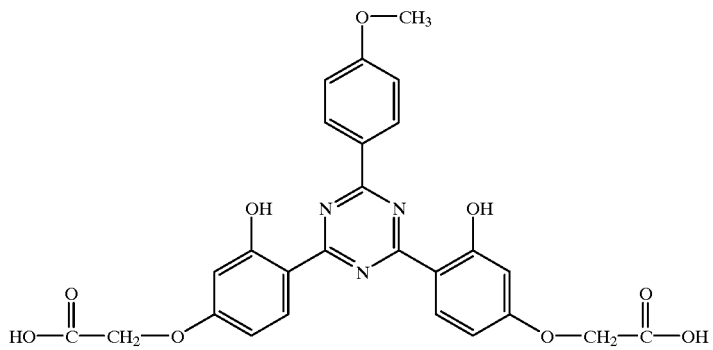

(104b)

EXAMPLE 4c

The compound of formula (104b) is dissolved in methoxyethanol, and 2 equivalents of triethanolamine are added thereto. Concentration of the solution by evaporation yields the compound of formula

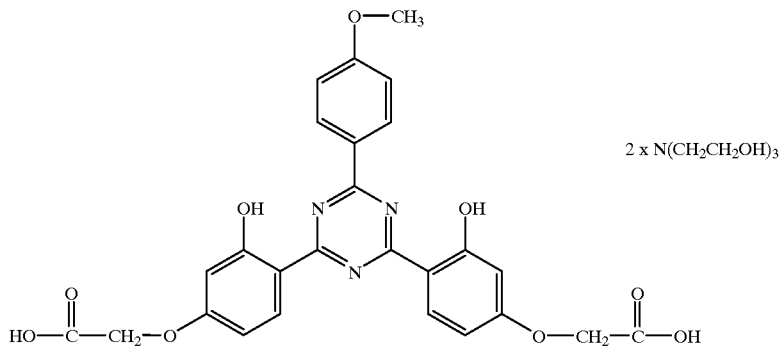

(104c)

Spectral data of the compound of formula (104c):

UV spectrum in water:

$\lambda_{max1}$=340 nm; $\epsilon$=34268

$\lambda_{max2}$=325 nm; $\epsilon$=36973

EXAMPLE 4d 11.5 g of the compound of formula (104c) are suspended in 50 ml of N,N-dimethylamino-propylamine; sodium methanolate is added and the mixture is stirred at 130° C. under a stream of $N_2$ for 16 hours. Concentration of the reaction mass by evaporation yields the compound of formula

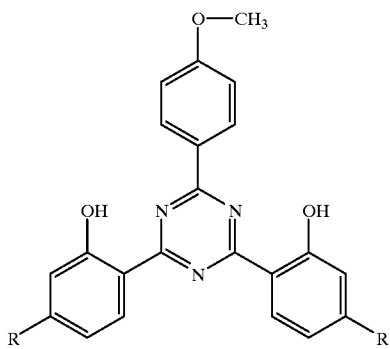

(104d)

-continued

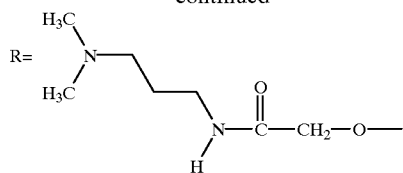

EXAMPLE 4e 6 g of the compound of formula (104d) are stirred in 50 ml of dioxane with chloroacetamide at 75° C. for 12 hours. Concentration of the reaction mass by evaporation and extraction of the crude product with acetone yield 7.1 g of the compound of formula

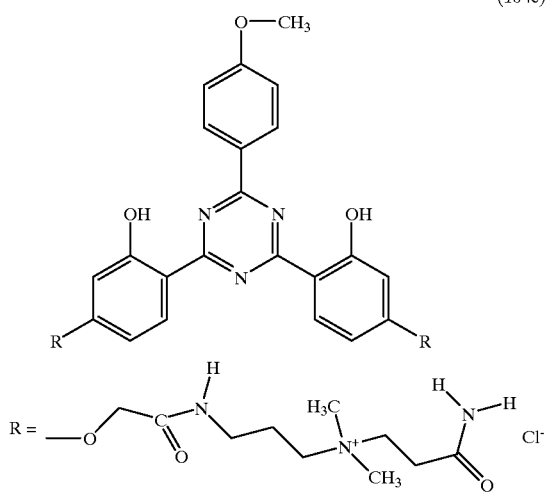

(104e)

Spectral data:
UV spectrum in ethanol:

$\lambda_{max}$ 339 nm; $\epsilon$=36803
$\lambda_{max}$ 320 nm: $\epsilon$=32104

EXAMPLE 4f 6 g of the compound of formula (104e) are reacted in 50 ml of dioxane with 2.64 g of dimethyl sulfate at 75° C. Concentration of the reaction mass by evaporation and extraction of the crude product with acetone yield 7.2 g of the compound of formula

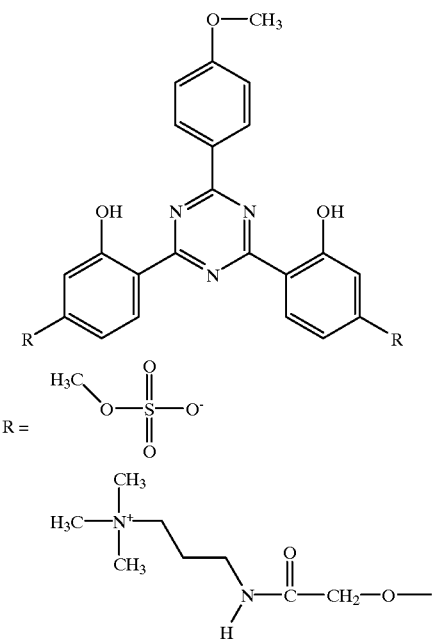

(104f)

Spectral data:

UV spectrum in water:

$\lambda_{max1}$ 328 nm; $\epsilon$=31763
$\lambda_{max1}$ 306 nm; $\epsilon$=30836

EXAMPLE 5

In accordance with Example 4a, 40.4 g of 2,4-bis(2,4-dihydroxyphenyl)-6-(4-methoxyphenyl)-1,3,5-triazine are reacted with 137 g of D,L-α-tocopherol chloroacetate (prepared as tocopherol and acetyl chloride in pyridine/acetone). Working up the reaction mass by crystallisation from methyl ethyl ketone yields 84 g of the compound of formula (105)

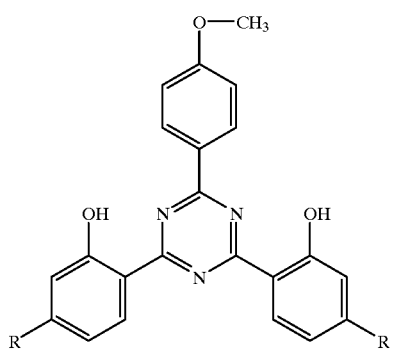

-continued

R = 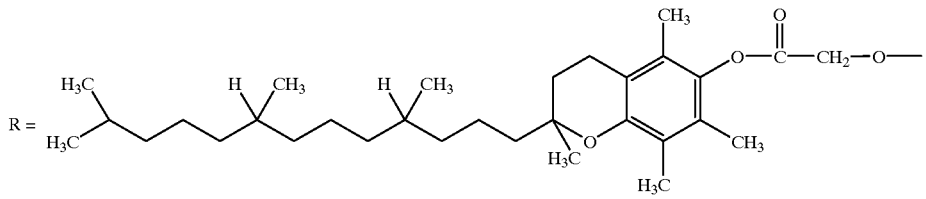

Spectral data
UV spectrum in dioxane:
$\lambda_{max1}$ 336 nm; $\epsilon$=45999
$\lambda_{max2}$ 306 nm; $\epsilon$=43748

Application Example

EXAMPLE 6
Preparation of a Sunscreen Lotion (W/O)

| A | caprylic/capric triglyceride | 6.0% |
|---|---|---|
|   | octyldodecanol | 4.0% |
|   | cetearyl isononanoate | 3.0% |
|   | polyglyceryl-2 dipolyhydroxystearate | 3.0% |
|   | glyceryl oleate | 1.0% |
|   | cera alba | 2.0% |
| B | $C_{12-15}$alkyl benzoate | 4.0% |
|   | octylmethoxycinnamate | 4.5% |
|   | compound of formula (105) | 0.5% |
| C | water | 58.5% |
|   | 86% glycerol | 5.0% |
|   | preservative | 0.5% |
| D | micronised 2,2'-methylene-bis(6-(2H-benzotriazol-2-yl)-4-(1,1,3,3-tetramethylbutyl)-phenol (50% suspension in water) | 8.0 % |

The components of part A are heated to 75–80° C. and part B, premixed at 80° C., is added with stirring. The components of part C are heated to about 80–90° C. and, with vigorous stirring, homogenised into part A+B. With slow stirring, the mixture is allowed to cool to room temperature and part D is stirred in homogeneously.

The sunscreen lotion exhibits effective cosmetic light-stabilisation.

EXAMPLE 7
Preparation of a Sunscreen Lotion (O/W)

| A | polyglyceryl-3 methylglucose distearate | 2.0% |
|---|---|---|
|   | decyl oleate | 5.7% |
|   | isopropyl palmitate | 5.0% |
|   | caprylic/capric triglyceride | 1.5% |
|   | octylmethoxycinnamate | 6.0% |
| B | water | 68.9% |
|   | compound of formula (104c) | 5.5% |
|   | 86% glycerol | 3.5% |
|   | preservative | 0.5% |
| C | carbomer | 0.2% |
|   | isopropyl palmitate | 0.8% |
| D | 10% sodium hydroxide | 0.4% |

The components of parts A and B are each heated to about 80° C. and carefully stirred together. Then the components of part C are added and homogenised. After cooling, part D is added with stirring.

The sunscreen lotion exhibits effective cosmetic light-stabilisation.

EXAMPLE 8
Preparation of a Hair Conditioner Having UV Protection (Foam)

| A | water | 83.3% |
|---|---|---|
|   | Nonoxynol 9 | 0.3% |
|   | oleth 20 | 0.5% |
|   | PVP/VA copolymer | 4.0% |
|   | compound of formula (104f) | 5.0% |
|   | Polyquaternium-11 | 5.0% |
| B | lauryl acetate | 0.5% |
|   | polyglyceryl-2 dipolyhydroxystearate | 1.0% |
| C | preservative | 0.5% |

The components of parts A and B are mixed together at about 50° C. and, after cooling, part C and perfume oil, as required, are added. The mixture is introduced into an aerosol container and propellant is added.

What is claimed is:
1. A resorcinyl-triazine of formula

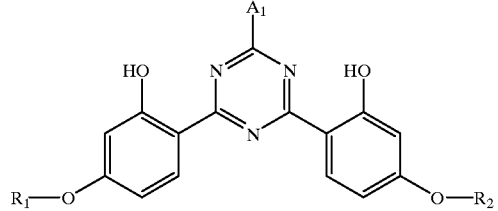

(1)

wherein $R_1$ and $R_2$ are each independently of the other a radical of formula (1a)

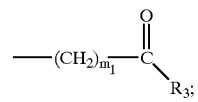

$R_3$ is amino; mono- or di-$C_1$–$C_5$alkylamino; a radical of formula

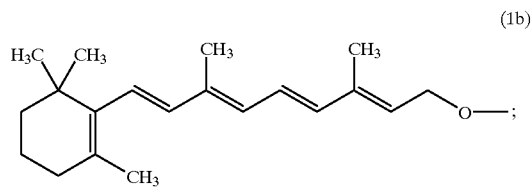

(1b)

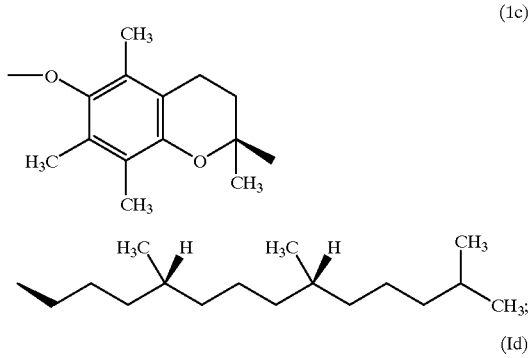
(1c)

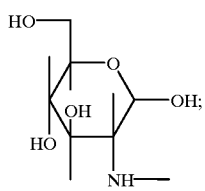
(1d)

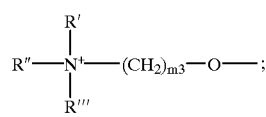
(1e)

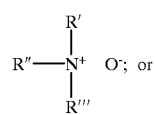
(1f)

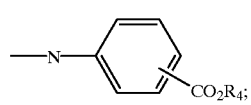
(1g)

wherein R', R" and R'" are each independently of the others $C_1$–$C_{14}$alkyl that is unsubstituted or substituted by one or more OH groups;

$R_4$ is hydrogen; M; $C_1$–$C_5$alkyl; or a radical of formula —(CH$_2$)$_{m_2}$—O—$T_1$;

$A_1$ is a radical of formula (1g);

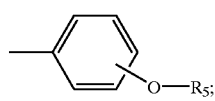
(1h)

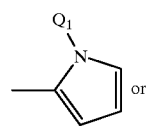
(1i)

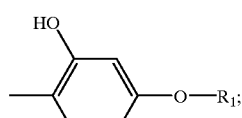
(1k)

$R_5$ is hydrogen; $C_1$–$C_{10}$alkyl, —(CH$_2$CHR$_6$—O)$_{n_1}$—R$_4$, or a radical of formula —CH$_2$—CH(—OH)—CH$_2$—O—T$_1$;

$R_6$ is hydrogen; or methyl;

$T_1$ is hydrogen; or $C_1$–$C_8$alkyl;

$Q_1$ is $C_1$–$C_{18}$alkyl;

M is a metal cation;

$m_1$ is from 1 to 3; and $m_2$ is from 1 to 4;

$m_3$ is from 2 to 14; and $n_1$ is 1–16.

2. A resorcinyl-triazine according to claim 1, wherein $A_1$ is a radical of formula

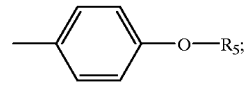
(1h$_1$)

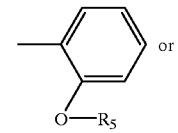
(1h$_2$)

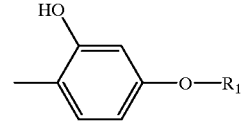
(1k$_1$)

wherein $R_1$ and $R_5$ are as defined in claim 1.

3. A resorcinyl-triazine according to claim 1 of formula

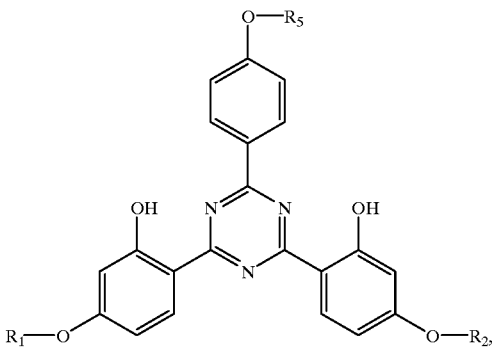
(2)

wherein $R_1$ and $R_2$ are each independently of the other a radical of the formula

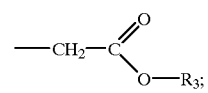

$R_3$ is hydrogen; or $C_1$–$C_5$alkyl; and $R_5$ is $C_1$–$C_{10}$alkyl.

4. A resorcinyl-triazine according to claim 1 of formula

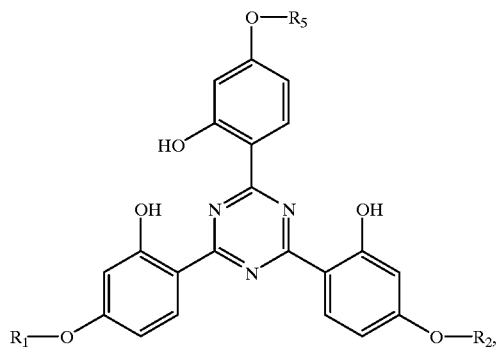
(3)

wherein $R_1$, $R_2$ and $R_5$ are each independently of the others a radical of formula

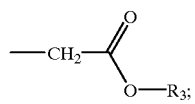

and $R_3$ is hydrogen; or $C_1$–$C_5$alkyl.

5. A resorcinyl-triazine according to claim 4, wherein $R_1$, $R_2$ and $R_5$ have the same meaning.

6. A process for the preparation of a resorcinyl-triazine of formula (1) according to claim 1 wherein $A_1$ is a radical of formula (1a) and $R_1$ and $R_2$ have the same meaning, by reaction of the appropriate phenylmagnesium bromide compound in a Grignard reaction with cyanuric chloride to form a dichlorotriazine compound of formula

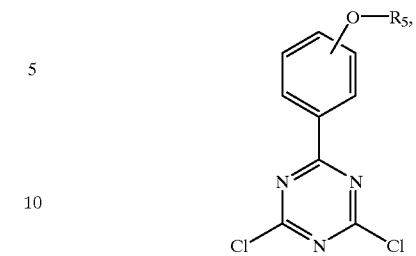
(II)

introduction of the resorcinol groups by Friedel-Crafts acylation of resorcinol in the presence of a Lewis acid, and etherification of the free, p-positioned hydroxy groups, depending upon the meaning of the radicals $R_1$ and $R_2$, by alkylation or acid-catalysed addition of glycidyl ethers.

7. A cosmetic composition which comprises at least one compound of the formula

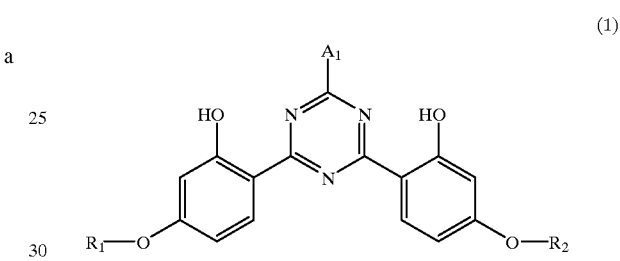
(1)

wherein $R_1$ and $R_2$ are each independently of the other a radical of formula (1a)

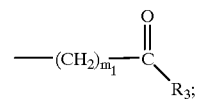

$R_3$ is hydroxy; $C_1$–$C_5$alkyl that is unsubstituted or substituted by one or more OH groups; $C_1$–$C_5$alkoxy; amino; mono- or di-$C_1$–$C_5$alkylamino; OM; a radical of the formula

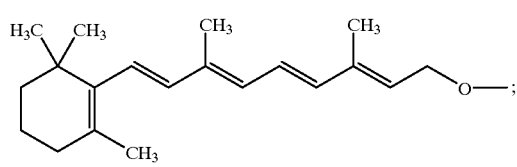
(1b)

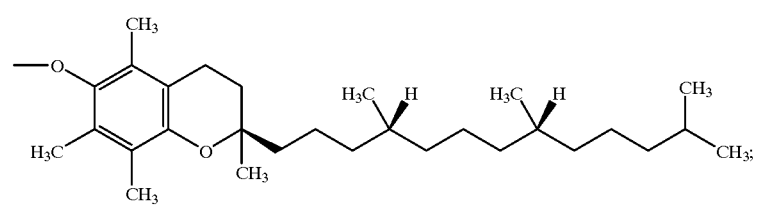
(1c)

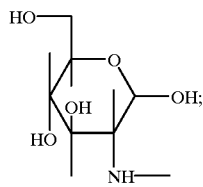

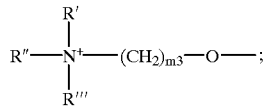

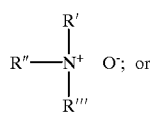

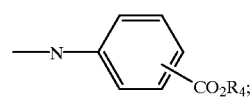

wherein R', R" and R'" are each independently of the others $C_1$–$C_{14}$alkyl that is unsubstituted or substituted by one or more OH groups;

$R_4$ is hydrogen; M; $C_1$–$C_5$alkyl; or a radical of formula —$(CH_2)_{m_2}$—O—$T_1$;

$A_1$ is a radical of the formula (1g);

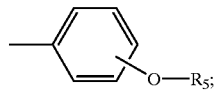

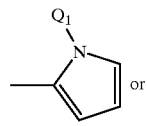

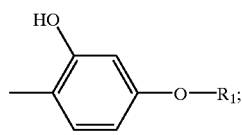

$R_5$ is hydrogen; $C_1$–$C_{10}$alkyl, —$(CH_2CHR_6$—O$)_{n_1}$—$R_4$, or a radical of formula —$CH_2$—CH(—OH)—$CH_2$—O—$T_1$;

$R_6$ is hydrogen; or methyl;

$T_1$ is hydrogen; or $C_1$–$C_8$alkyl;

$Q_1$ is $C_1$–$C_{18}$alkyl;

M is a metal cation;

$m_1$ is from 1 to 3 ;

$m_2$ is from 1 to 4 ;

$m_3$ is from 2 to 14; and $n_1$ is 1–16;

with cosmetically acceptable carriers or auxiliaries.

8. A composition according to claim 7, additionally comprising UV screening agents which are not of the formula (1).

9. A composition according to claim 8, comprising as further UV screening agents triazines, oxanilides, triazoles, vinyl-group-containing amides or cinnamic acid amides.

* * * * *